US012570729B2

(12) United States Patent
    Kumar Banerjee

(10) Patent No.: US 12,570,729 B2
(45) Date of Patent: Mar. 10, 2026

(54) ANTIBODY FRAGMENT BASED ANTIFUNGAL CONJUGATE SELECTIVELY TARGETING CANDIDA

(71) Applicant: ABGENICS LIFESCIENCES PRIVATE LIMITED, Pune (IN)

(72) Inventor: Sanjiban Kumar Banerjee, Pune (IN)

(73) Assignee: ABGENICS LIFESCIENCES PRIVATE LIMITED, Pune (IN)

( * ) Notice: Subject to any disclaimer, the term of this patent is extended or adjusted under 35 U.S.C. 154(b) by 569 days.

(21) Appl. No.: 17/998,347

(22) PCT Filed: May 16, 2021

(86) PCT No.: PCT/IB2021/054188
    § 371 (c)(1),
    (2) Date: Nov. 9, 2022

(87) PCT Pub. No.: WO2021/234527
    PCT Pub. Date: Nov. 25, 2021

(65) Prior Publication Data
    US 2024/0092878 A1      Mar. 21, 2024

(30) Foreign Application Priority Data
    May 17, 2020   (IN) .............................. 202021020768

(51) Int. Cl.
    *C07K 16/14*          (2006.01)
    *A61K 38/17*          (2006.01)
(52) U.S. Cl.
    CPC .......... *C07K 16/14* (2013.01); *A61K 38/1709* (2013.01); *C07K 2317/22* (2013.01); *C07K 2317/569* (2013.01)
(58) Field of Classification Search
    CPC ................ C07K 16/14; C07K 2317/22; C07K 2317/569; A61K 38/1709
    See application file for complete search history.

(56) References Cited

U.S. PATENT DOCUMENTS

| 2003/0143234 A1 | 7/2003 | Shi et al. |
| 2014/0364595 A1 | 12/2014 | Bapat et al. |

FOREIGN PATENT DOCUMENTS

| WO | WO2003007989 A1 * | 1/2003 | ............. A61K 39/40 |

OTHER PUBLICATIONS

Tso et al. 2018 (The Elusive Anti-Candida Vaccine: Lessons from the Past and Opportunities for the Future; Frontiers in Immunology 9(897): 1-13) (Year: 2018).*

* cited by examiner

*Primary Examiner* — Mary Maille Lyons
(74) *Attorney, Agent, or Firm* — Mainline Intellectual Property; Syam Anand

(57) ABSTRACT

The present invention provides a novel antibody fragment based antifungal conjugate selectively targeting *Candida* spp. comprising of at least one antimicrobial peptide at one end of the conjugate, more particularly, human Histatin-5; an antibody fragment at the other end of the conjugate, specific against *Candida* spp. enolase, a virulence factor protease and biofilm specific antigen of *Candida* spp.; at least one signal protease cleavage sequence susceptible to cleavage by virulent protease secreted by *Candida* spp., secreted aspartyl proteinase-1 (SAP1); and at least one flexible polypeptide linker. The signal protease cleavage sequence and the flexible polypeptide linker are in tandem with each other and placed in between the antimicrobial peptide and the antibody. The in vitro MIC-99 of the conjugate against *Candida* spp., is in the range of 0.2-0.3 µM, more specifically, 0.25 µM or 250 nM.

4 Claims, 4 Drawing Sheets

Figures 1A, 1B, 1C, 1D:
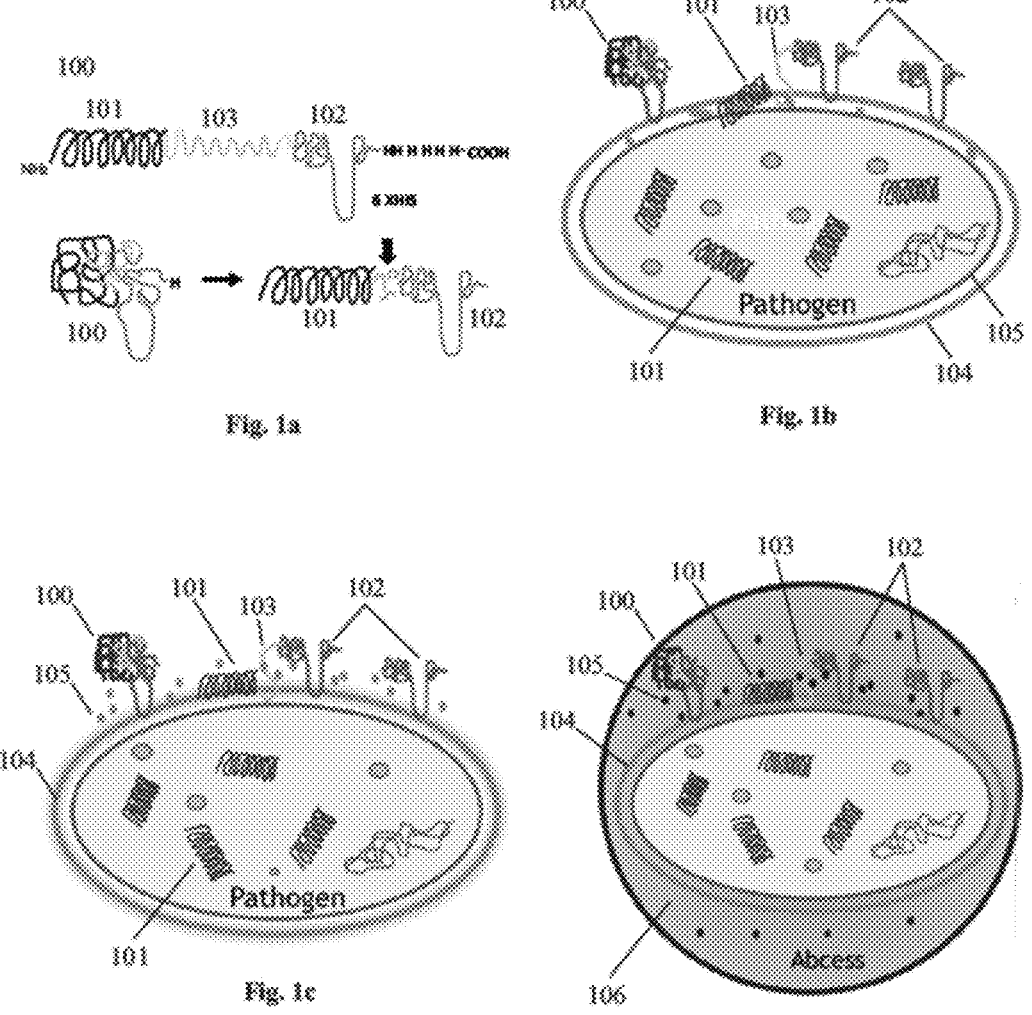

Specification includes a Sequence Listing.

Seq. ID 20

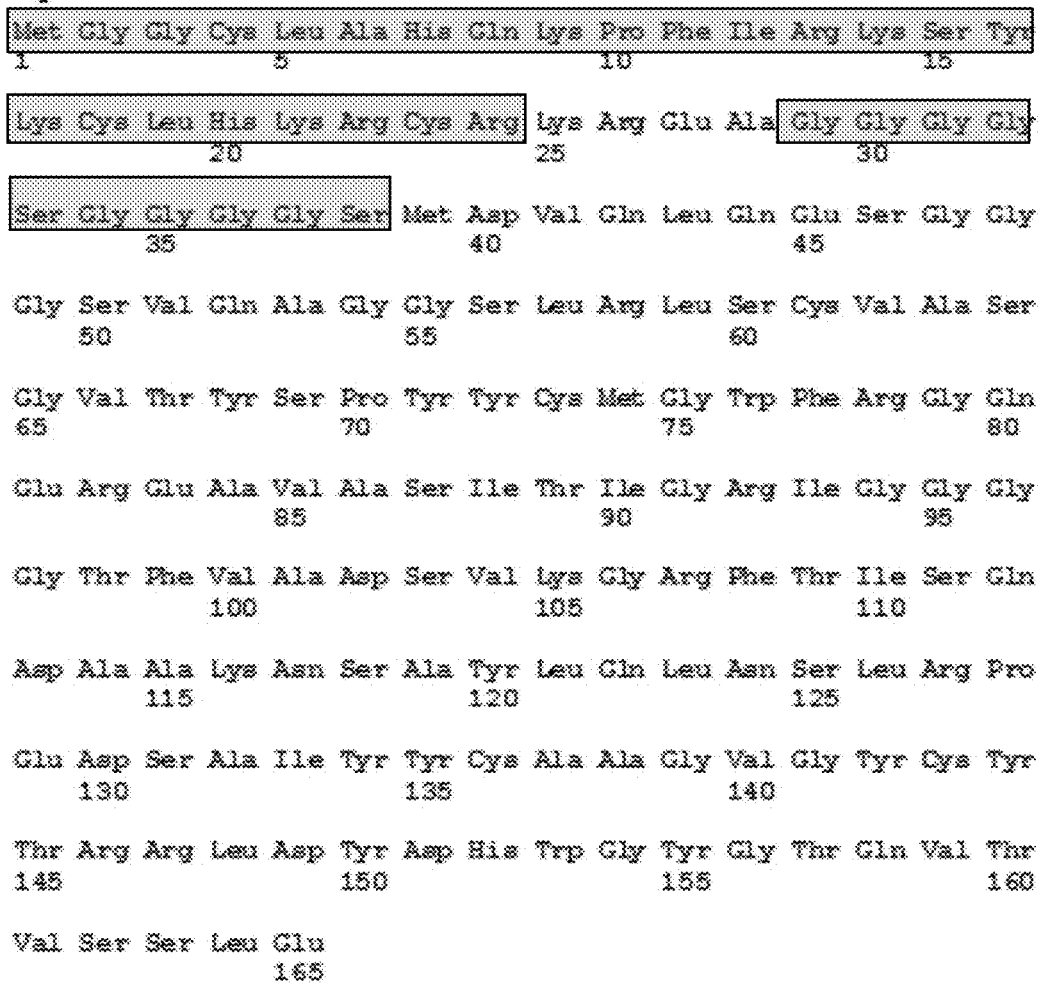

| Met | Gly | Gly | Cys | Leu | Ala | His | Gln | Lys | Pro | Phe | Ile | Arg | Lys | Ser | Tyr |
| 1 | | | | 5 | | | | | 10 | | | | | 15 | |

| Lys | Cys | Leu | His | Lys | Arg | Cys | Arg | Lys | Arg | Glu | Ala | Gly | Gly | Gly | Gly |
| | | | 20 | | | | | 25 | | | | | 30 | | |

| Ser | Gly | Gly | Gly | Gly | Ser | Met | Asp | Val | Gln | Leu | Gln | Glu | Ser | Gly | Gly |
| | | 35 | | | | | 40 | | | | | 45 | | | |

| Gly | Ser | Val | Gln | Ala | Gly | Gly | Ser | Leu | Arg | Leu | Ser | Cys | Val | Ala | Ser |
| | 50 | | | | | 55 | | | | | 60 | | | | |

| Gly | Val | Thr | Tyr | Ser | Pro | Tyr | Tyr | Cys | Met | Gly | Trp | Phe | Arg | Gly | Gln |
| 65 | | | | | 70 | | | | | 75 | | | | | 80 |

| Glu | Arg | Glu | Ala | Val | Ala | Ser | Ile | Thr | Ile | Gly | Arg | Ile | Gly | Gly | Gly |
| | | | | 85 | | | | | 90 | | | | | 95 | |

| Gly | Thr | Phe | Val | Ala | Asp | Ser | Val | Lys | Gly | Arg | Phe | Thr | Ile | Ser | Gln |
| | | | 100 | | | | | 105 | | | | | 110 | | |

| Asp | Ala | Ala | Lys | Asn | Ser | Ala | Tyr | Leu | Gln | Leu | Asn | Ser | Leu | Arg | Pro |
| | | 115 | | | | | 120 | | | | | 125 | | | |

| Glu | Asp | Ser | Ala | Ile | Tyr | Tyr | Cys | Ala | Ala | Gly | Val | Gly | Tyr | Cys | Tyr |
| | 130 | | | | | 135 | | | | | 140 | | | | |

| Thr | Arg | Arg | Leu | Asp | Tyr | Asp | His | Trp | Gly | Tyr | Gly | Thr | Gln | Val | Thr |
| 145 | | | | | 150 | | | | | 155 | | | | | 160 |

| Val | Ser | Ser | Leu | Glu |
| | | | | 165 |

Fig. 2b

SEQUENCE LISTING

```
<160> NUMBER OF SEQ ID NOS: 20

<210> SEQ ID NO 1
<211> LENGTH: 16
<212> TYPE: PRT
<213> ORGANISM: Homo sapiens
```

```
<220> FEATURE:
<221> NAME/KEY: MISC_FEATURE
<223> OTHER INFORMATION: "x" is any amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

<400> SEQUENCE: 1

Met Xaa Ala Lys Arg His His Gly Tyr Lys Arg Lys Phe His Xaa Xaa
1               5                   10                  15

<210> SEQ ID NO 2
<211> LENGTH: 12
<212> TYPE: PRT
<213> ORGANISM: Homo sapiens

<400> SEQUENCE: 2

Ala Lys Arg His His Gly Tyr Lys Arg Lys Phe His
1               5                   10

<210> SEQ ID NO 3
<211> LENGTH: 24
<212> TYPE: PRT
<213> ORGANISM: Homo sapiens
<220> FEATURE:
<221> NAME/KEY: MISC_FEATURE
<223> OTHER INFORMATION: "x" is any amino acid
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 3

Xaa Xaa Leu Ala His Gln Lys Pro Phe Ile Arg Lys Ser Tyr Lys Cys
1               5                   10                  15

Leu His Lys Arg Cys Arg Xaa Xaa
            20

<210> SEQ ID NO 4
<211> LENGTH: 22
<212> TYPE: PRT
<213> ORGANISM: Homo sapiens

<400> SEQUENCE: 4

Gly Cys Leu Ala His Gln Lys Pro Phe Ile Arg Lys Ser Tyr Lys Cys
1               5                   10                  15

Leu His Lys Arg Cys Arg
            20

<210> SEQ ID NO 5
<211> LENGTH: 41
<212> TYPE: PRT
<213> ORGANISM: Homo sapiens

<400> SEQUENCE: 5

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
```

```
                20              25              30

Pro Gly Thr Lys Cys Cys Lys Lys Pro
        35              40

<210> SEQ ID NO 6
<211> LENGTH: 130
<212> TYPE: PRT
<213> ORGANISM: Camelus dromedarius

<400> SEQUENCE: 6

Met Ala Asp Val Gln Leu Gln Glu Ser Gly Gly Gly Ser Val Gln Ala
1               5                   10                  15

Gly Gly Ser Leu Arg Leu Ser Cys Thr Ile Ser Gly Tyr Ser Gly Tyr
            20                  25                  30

Ser Phe Arg Thr Leu Cys Val Tyr Trp Phe Arg Gln Ala Pro Gly Lys
        35                  40                  45

Glu Arg Glu Gly Val Ala Arg Ile Asn Ile Gly Ser Thr Ser Thr Tyr
    50                  55                  60

Tyr Gly Asp Ser Val Lys Gly Arg Phe Thr Val Ser Ser Asp Asn Asp
65                  70                  75                  80

Lys Asn Thr Val Tyr Leu Glu Met Asn Ser Leu Glu Pro Glu Asp Thr
                85                  90                  95

Val Thr Tyr Tyr Cys Ala Ala Gln Pro Asn Tyr Cys Tyr Leu Phe Ser
            100                 105                 110

Tyr Ser Asn Lys Leu Thr Tyr Trp Gly Gln Gly Thr Gln Val Thr Val
        115                 120                 125

Ser Ser
    130

<210> SEQ ID NO 7
<211> LENGTH: 115
<212> TYPE: PRT
<213> ORGANISM: Camelus dromedarius

<400> SEQUENCE: 7

Met Asp Val Gln Leu Gln Glu Ser Gly Gly Gly Leu Val Gln Pro Gly
1               5                   10                  15

Gly Ser Leu Arg Leu Ser Cys Ala Thr Ser Gly Phe Thr Phe Asn Ser
            20                  25                  30

Tyr Trp Met Tyr Trp Val Arg Gln Ala Pro Gly Lys Gly Pro Glu Trp
        35                  40                  45

Val Ala Arg Ile Asn Thr Arg Thr Pro Arg Ile Thr Tyr Thr Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Thr Thr Asn Arg Asn Arg Val Val Gly Gly Gly Thr Gln Val Thr
            100                 105                 110

Val Ser Ser
        115

<210> SEQ ID NO 8
<211> LENGTH: 125
<212> TYPE: PRT
<213> ORGANISM: Camelus dromedarius

<400> SEQUENCE: 8
```

```
Met Asp Val Gln Leu Gln Glu Ser Gly Gly Gly Ser Val Gln Ala Gly
1               5                   10                  15

Gly Ser Leu Arg Leu Ser Cys Val Ala Ser Gly Val Thr Tyr Ser Pro
            20                  25                  30

Tyr Tyr Cys Met Gly Trp Phe Arg Gly Gln Glu Arg Glu Ala Val Ala
        35                  40                  45

Ser Ile Thr Ile Gly Arg Ile Gly Gly Gly Thr Phe Val Ala Asp
    50                  55                  60

Ser Val Lys Gly Arg Phe Thr Ile Ser Gln Asp Ala Ala Lys Asn Ser
65                  70                  75                  80

Ala Tyr Leu Gln Leu Asn Ser Leu Arg Pro Glu Asp Ser Ala Ile Tyr
                85                  90                  95

Tyr Cys Ala Ala Gly Val Gly Tyr Cys Tyr Thr Arg Arg Leu Asp Tyr
            100                 105                 110

Asp His Trp Gly Tyr Gly Thr Gln Val Thr Val Ser Ser
        115                 120                 125
```

```
<210> SEQ ID NO 9
<211> LENGTH: 129
<212> TYPE: PRT
<213> ORGANISM: Camelus dromedarius

<400> SEQUENCE: 9
```

```
Met Asp Val Gln Leu Gln Glu Ser Gly Gly Gly Ser Val Gln Ala Gly
1               5                   10                  15

Gly Ser Leu Arg Leu Ser Cys Thr Ile Ser Gly Tyr Ser Gly Tyr Ser
            20                  25                  30

Phe Arg Thr Leu Cys Val Tyr Trp Phe Arg Gln Ala Pro Gly Lys Gly
        35                  40                  45

Leu Glu Gly Val Ala Arg Ile Asn Ile Gly Ser Thr Ser Thr Tyr Tyr
    50                  55                  60

Gly Asp Ser Val Lys Gly Arg Phe Thr Val Ser Ser Asp Asn Asp Lys
65                  70                  75                  80

Asn Thr Val Tyr Leu Glu Met Asn Ser Leu Glu Pro Glu Asp Thr Val
                85                  90                  95

Thr Tyr Tyr Cys Ala Ala Gln Pro Asn Tyr Cys Tyr Leu Phe Ser Tyr
            100                 105                 110

Ser Asn Lys Leu Thr Tyr Trp Gly Gln Gly Thr Gln Val Thr Val Ser
        115                 120                 125

Ser
```

```
<210> SEQ ID NO 10
<211> LENGTH: 5
<212> TYPE: PRT
<213> ORGANISM: Artificial Sequence
<220> FEATURE:
<223> OTHER INFORMATION: SAP1 cleavage sequence

<400> SEQUENCE: 10
```

```
Glu Leu Tyr Leu Val
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: SAP1 cleavage sequence
```

```
<400> SEQUENCE: 11

Leu Val Glu Leu Leu Tyr Leu
1               5

<210> SEQ ID NO 12
<211> LENGTH: 4
<212> TYPE: PRT
<213> ORGANISM: Artificial Sequence
<220> FEATURE:
<223> OTHER INFORMATION: signal peptidase 3 cleavage seq

<400> SEQUENCE: 12

Lys Arg Glu Ala
1

<210> SEQ ID NO 13
<211> LENGTH: 13
<212> TYPE: PRT
<213> ORGANISM: Artificial Sequence
<220> FEATURE:
<223> OTHER INFORMATION: Neutrophil protease cleavage sequence

<400> SEQUENCE: 13

Asn Ala Thr Leu Asp Pro Arg Ser Phe Leu Leu Arg Asn
1               5                   10

<210> SEQ ID NO 14
<211> LENGTH: 5
<212> TYPE: PRT
<213> ORGANISM: Artificial Sequence
<220> FEATURE:
<223> OTHER INFORMATION: GS linker sequence

<400> SEQUENCE: 14

Gly Gly Gly Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: GS linker Sequence

<400> SEQUENCE: 15

Gly Gly Gly Gly Ser Gly Gly Gly Gly Ser
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Linker Sequence
<220> FEATURE:
<221> NAME/KEY: MISC_FEATURE
<223> OTHER INFORMATION: Glu can be Glu or Asp

<400> SEQUENCE: 16

Glu Glu Gly Glu Phe Ser Glu Ala Arg
1               5

<210> SEQ ID NO 17
<211> LENGTH: 17
<212> TYPE: PRT
<213> ORGANISM: Artificial Sequence
```

```
<220> FEATURE:
<223> OTHER INFORMATION: Linker Sequence

<400> SEQUENCE: 17

Gly Ser Ala Asp Asp Ala Lys Lys Asp Ala Ala Lys Lys Asp Gly Lys
1               5                   10                  15

Ser

<210> SEQ ID NO 18
<211> LENGTH: 20
<212> TYPE: PRT
<213> ORGANISM: Artificial Sequence
<220> FEATURE:
<223> OTHER INFORMATION: Linker Sequence

<400> SEQUENCE: 18

Ser Ser Ala Asp Asp Ala Lys Lys Asp Ala Ala Lys Lys Asp Asp Ala
1               5                   10                  15

Lys Lys Asp Ala
            20

<210> SEQ ID NO 19
<211> LENGTH: 155
<212> TYPE: PRT
<213> ORGANISM: Artificial Sequence
<220> FEATURE:
<223> OTHER INFORMATION: ANTIBODY FRAGMENT BASED ANTIFUNGAL CONJUGATE

<400> SEQUENCE: 19

Met Gly Ala Lys Arg His His Gly Tyr Lys Arg Lys Phe His Glu Leu
1               5                   10                  15

Tyr Leu Val Gly Gly Gly Gly Ser Met Asp Val Gln Leu Gln Glu Ser
            20                  25                  30

Gly Gly Gly Ser Val Gln Ala Gly Gly Ser Leu Arg Leu Ser Cys Thr
        35                  40                  45

Ile Ser Gly Tyr Ser Gly Tyr Ser Phe Arg Thr Leu Cys Val Tyr Trp
    50                  55                  60

Phe Arg Gln Ala Pro Gly Lys Gly Leu Glu Gly Val Ala Arg Ile Asn
65                  70                  75                  80

Ile Gly Ser Thr Ser Thr Tyr Tyr Gly Asp Ser Val Lys Gly Arg Phe
                85                  90                  95

Thr Val Ser Ser Asp Asn Asp Lys Asn Thr Val Tyr Leu Glu Met Asn
            100                 105                 110

Ser Leu Glu Pro Glu Asp Thr Val Thr Tyr Tyr Cys Ala Ala Gln Pro
        115                 120                 125

Asn Tyr Cys Tyr Leu Phe Ser Tyr Ser Asn Lys Leu Thr Tyr Trp Gly
    130                 135                 140

Gln Gly Thr Gln Val Thr Val Ser Ser Leu Glu
145                 150                 155

<210> SEQ ID NO 20
<211> LENGTH: 165
<212> TYPE: PRT
<213> ORGANISM: Artificial Sequence
<220> FEATURE:
<223> OTHER INFORMATION: ANTIBODY FRAGMENT BASED ANTIFUNGAL CONJUGATE

<400> SEQUENCE: 20

Met Gly Gly Cys Leu Ala His Gln Lys Pro Phe Ile Arg Lys Ser Tyr
1               5                   10                  15
```

-continued

```
Lys Cys Leu His Lys Arg Cys Arg Lys Arg Glu Ala Gly Gly Gly Gly
            20              25              30

Ser Gly Gly Gly Gly Ser Met Asp Val Gln Leu Gln Glu Ser Gly Gly
        35              40              45

Gly Ser Val Gln Ala Gly Gly Ser Leu Arg Leu Ser Cys Val Ala Ser
    50              55              60

Gly Val Thr Tyr Ser Pro Tyr Tyr Cys Met Gly Trp Phe Arg Gly Gln
65              70              75              80

Glu Arg Glu Ala Val Ala Ser Ile Thr Ile Gly Arg Ile Gly Gly Gly
            85              90              95

Gly Thr Phe Val Ala Asp Ser Val Lys Gly Arg Phe Thr Ile Ser Gln
            100             105             110

Asp Ala Ala Lys Asn Ser Ala Tyr Leu Gln Leu Asn Ser Leu Arg Pro
        115             120             125

Glu Asp Ser Ala Ile Tyr Tyr Cys Ala Ala Gly Val Gly Tyr Cys Tyr
    130             135             140

Thr Arg Arg Leu Asp Tyr Asp His Trp Gly Tyr Gly Thr Gln Val Thr
145             150             155             160

Val Ser Ser Leu Glu
            165
```

ANTIBODY FRAGMENT BASED ANTIFUNGAL CONJUGATE SELECTIVELY TARGETING CANDIDA

RELATED APPLICATIONS

This application claims priority from the PCT application No. PCT/IB2021/054188 filed on 16 of May 2021, which claims priority to the Indian provisional patent application numbered 202021020768 titled "AN ANTIBODY FRAGMENT BASED ANTIFUNGAL CONJUGATE SELECTIVELY TARGETING *CANDIDA*" filed on 17 of May 2020. Both applications are incorporated in full herein by reference.

REFERENCE TO SEQUENCE LISTING

A Sequence listing in text format is incorporated by reference into the specification. The name of the text filed containing the Sequence Listing is Seq. *Candida*_ST25. The test file is about 13 KB, and is being submitted electronically via EFS-WEB.

FIELD OF THE INVENTION

The present invention relates to an antibody fragment based antifungal conjugate selectively targeting *Candida* spp. More specifically, the antibody fragment based antifungal conjugate comprises of an antimicrobial peptide attached by a cleavable linker to and a heavy chain fragment of an antibody, targeting *Candida* spp. preferably, *C. albicans, C. tropicalis, C. krusei, C. parasilopsis,* and *C. glabrata.*

BACKGROUND OF THE INVENTION

*Candida* spp. are major human fungal pathogens that cause both mucosal and deep tissue infections. These yeasts are commensal in healthy humans and may cause systemic infection in immune compromised situations due to their great adaptability to different host niches. The genus is composed of heterogeneous group of organisms, and more than 17 different *Candida* spp. are known to be etiological agents of human infection. However, more than 70% of invasive infections are caused by *Candida albicans*, the incidences of non-*albicans* species are increasing (Delaloye J and Calandra T. Virulence. 2014; 5:161-9). Nearly 42% of HIV positive patients presented mixed oral infection by various *Candida* spp., with *C. albicans* and *C. glabrata, C. tropicalis,* and *C. krusei* having the most recurrent associations. Higher tissue damage in co-infection compared to single *C. albicans* infection, suggested a potential synergism between these species. Other *Candida* spp. like *C. parapsilopsis* has emerged as a significant nosocomial pathogen with clinical manifestations that include end ophthalmitis, endocarditis, septic arthritis, peritonitis and fungaemia, usually associated with invasive procedures or prosthetic devices. Candidaemia due to *C. tropicalis* has been associated with cancer, especially in patients with leukaemia. Candidaemia due to *C. glabrata* has been reported to be related to the use of fluconazole. *Candida* spp. is also associated with cutaneous candidiasis, vaginal infections, the urinary tract, and other anatomical sites and are most conducive to the development of infections in hospitalized patients (N. Papon, et al., 2103-PLoS pathogens September 9 (9) 1-4). Although associated with infections of bacterial origin, it is estimated that at least 10% have fungi as the principal etiological agent and that too is *Candida* spp.

Furthermore, the expanding population of immunocompromised patients who use intravenous catheters, total parenteral nutrition, invasive procedures and the increasing use of broad-spectrum antibiotics, cytotoxic chemotherapies and transplantation are some important factors that contribute to the increase of these infections. Biofilm production is also associated with a high level of antimicrobial resistance of the associated organisms. The ability of *Candida* spp. to form drug resistant biofilms is an important factor in their contribution to human disease (D S Perlin, et al., 2015, Current Clinical Microbiology Reports volume 2, pages 84-95). Biofilms prevent the access of the drugs to the pathogens and consequently these fungi become drug resistant which increases the morbidity and mortality of the infected patients. *C. albicans* can form biofilms on almost any medical device. The most involved systemic devices colonized by formation of such biofilms include vascular and urinary catheters, joint prostheses, cardiac valves, artificial vascular bypass devices, pacemakers, ventricular assist devices and central nervous system shunts.

Drug resistance frequently seen in *Candida* spp., are classified into two important classes: a) multiple drug resistant (MDR) fungi which is an isolate non-susceptible to ≥1 agent in ≥2 drug classes, and b) extensively drug resistant (XDR) fungi which is non susceptible to ≥1 agent in ≥3 drug classes. MDR and XDR fungi are quite common now a days (Ewa Ksiezopolska and Toni Gabaldón, Genes 2019, September 9 (9), 461). Antifungal resistance is less common in *C. albicans* but has been reported with long-term antifungal use and with recurrent infections, such as those with chronic mucocutaneous candidiasis or recurrent oropharyngeal candidiasis in patients with uncontrolled human immunodeficiency virus infection. Several of the non-*albicans Candida* spp., such as *C. krusei*, are intrinsically resistant or less susceptible to several classes of antifungals, whereas others, including *C. glabrata*, develop acquired resistance following exposure to antifungal agents. A new *Candida* spp., *C. auris* (Anna Jeffery-Smith et al. 2018 Clinical microbiology reviews 3111-18), that is naturally multidrug resistant is posing a serious threat to health care establishments across the globe and is rapidly becoming uncontrollable with the current therapy options.

There are only four classes of drugs that are available for systemic treatment of *Candida* infections including the azoles (fluconazole, itraconazole, isavuconazole, posaconazole, and voriconazole), polyenes (conventional amphotericin B and its lipid formulations), echinocandins (anidulafungin, caspofungin, and micafungin), and, finally, the pyrimidine analogue flucytosine. Among these drug classes, only members of the first three are licensed for monotherapy against *Candida* infections and only fluconazole and echinocandins are recommended as first line agents for invasive candidiasis.

The rise of multi-drug resistant pathogens has challenged researchers around the globe to come with novel solutions for killing pathogens and inhibiting/delaying the developmental process of mutagenic resistance in pathogens.

A class of antimicrobial molecules that has emerged as a solution is antimicrobial peptides. There have been efforts towards achieving target-specific antimicrobial therapy consisting of conjugating antibiotics to monoclonal antibodies or constructing large fusion proteins with antimicrobial recognition domains. These antibody-antibiotic conjugates enhance the therapeutic index by maximizing efficacy and minimizing off-target toxicity. Such conjugates comprise a targeting antibody covalently attached through a linker unit to a cytotoxic drug moiety.

U.S. Pat. No. 5,486,503A describes a composition for treating fungal infection comprising of amino acid sequences of naturally occurring human and macaque histatins. However, use of histatins directly without target specificity leads to unwanted toxicity in humans.

EP2039369A1 describes a composition comprising an antibody specific for at least one epitope of hsp90 from an organism of the *Aspergillus* genus, and caspofungin which is a lipopeptide antifungal drug. This antibody and drug combination targets *Aspergillus* spp.

CN103857440A provides conjugate-based antifungal or antibacterial prodrugs formed by coupling at least one antifungal agent or antibacterial agent with at least one linker and/or carrier. The prodrugs are of formula: (i) (AFA)m-X-(L)n; (ii) [(AFA)m'-X]p-L; (iii) AFA-[X-(L)n']q; or (iv) (AFA)m''-X, wherein: AFA is an antifungal agent or an antibacterial agent; L is a carrier; X is a linker; m ranges from 1 to 10; n ranges from 2 to 10; m' is 1 to 10; p is 1 to 10; n' is 1 to 10; and q is 1 to 10, provided that q' and n are not both 1; and m'' is 1 to 10. The prodrug is a conjugate of antifungal agent and linker sequence which is a carrier molecule specific to target microbe. The prodrug has a linker susceptible to cleavage by esterases. The prodrug conjugate is formulated into nanoparticles selected from the group comprising of liposome, polymeric nanoparticles, nano-emulsions, from micro-emulsifying drug delivery systems (SMEDDS), solid-lipid nanoparticles, nanostructured liquid, and any combination thereof. The size of the nanoparticle formulation is in the range of 20 nm to 500 nm. The major issue with such conjugate compositions is instability due to large size and high cost of production.

Recently there has been development of conjugates of microbe specific antibody and antimicrobial agent for increasing target specificity.

U.S. Pat. No. 4,867,973A is one of the earliest citations related to antibody-therapeutic agent conjugate. The invention is related to antibody-therapeutic agent conjugates having a therapeutic agent covalently attached to an antibody or antibody fragment.

Use of whole antibody makes the molecule bulky which led to use of camelid antibodies instead of normal immunoglobulins. It has been demonstrated that, in Camelidae family (camels, dromedarius, llamas and alpacas), about 50% of immunoglobulins are antibodies devoid of light chain. These heavy-chain antibodies interact with the antigen by the virtue of only one single variable domain, referred to as VHH(s), VHH domain(s) or VHH antibody (ies), or nanobodies. Despite the absence of light chain, these homo-dimeric antibodies exhibit a broad antigen-binding repertoire by enlarging their hypervariable regions. Recombinant VHH domains (VHHs) exhibit the antigen-binding capacity of the camelid original heavy-chain antibody (Nguen et al., 2001, Adv. Immunol., 79, 261-96; Myuldermans et al., 2001, Trends in Biochemical Sciences, 26:230-235). Small size (14-17 kDa) and increased plasticity appear to provide VHHs with unique potentialities: for instance, their diffusion into tissues is facilitated by their small size, and several VHHs are capable of inhibiting enzymatic activity by interacting with the active site cavity of enzymes such as alpha-amylase, carbonic anhydrase and hen egg lysozyme (Desmyter et. al., 1996, Nature Structural Biology, 3:803-11; Lauereys et. al., 1998, Embo J., 17:3512-20).

US20060211088A1 describes a method for generating or cloning a nucleic acid or nucleotide sequence that encodes a heavy chain antibody or an antigen-binding fragment directed against a specific antigen by providing a sample or population of cells from a Camelid immunized with said antigen, isolating from said sample or population said at least one cell that expresses or is capable of expressing a heavy chain antibody directed against said antigen, and obtaining from said at least one cell a nucleic acid or nucleotide sequence that encodes a heavy chain antibody directed against antigen or that encodes an antigen-binding fragment thereof directed against said antigen.

However, such antibody-drug conjugates have been successfully designed against bacteria, and so far, there are no reports of efficient antibody based antifungal conjugate. Moreover, in comparison to the development of new anti-microbials targeting bacteria, antifungal drug development faces a key fundamental challenge in that fungal pathogens are more closely related to the host. Consequently, many small molecules that are toxic to yeast are also toxic to humans.

The prior art does not provide a comprehensive solution to target fungal infections with high specificity and less toxicity to infected hosts. Moreover, the prior art fails to provide a simple solution for dealing with *Candida* spp. infection.

OBJECT(S) OF THE INVENTION

Accordingly, the present invention takes into account the drawbacks of the prior art and provides an invention with the main object of the invention providing a novel antibody fragment based antifungal conjugate selectively targeting *Candida* spp. which is capable to bind to biofilms produced by *Candida* spp. thereby increasing the efficacy of the antibody fragment based antifungal conjugate against *Candida* spp.; the antibody fragment based antifungal conjugate comprising of at least one antimicrobial peptide at one end of the conjugate either on the C or the N terminal end, preferably antimicrobial peptide belonging to the group comprising cationic histidine-rich antimicrobial peptides, mucin family of proteins, or human defensins; an antibody fragment at the other end of the conjugate, preferably a camelid heavy chain antibody variable region fragment (VHH), specific against the antigen of *Candida* spp. selected from the group consisting surface antigen, and extracellular matrix antigen responsible for pathogenicity and biofilm formation; a signal protease cleavage sequence; and a flexible polypeptide linker in tandem placed between the antimicrobial peptide and antibody fragment, wherein, the signal protease cleavage sequence is susceptible to cleavage by proteases belonging to the group consisting of membrane proteases, cell wall associated proteases, and secreted proteases of *Candida* spp., and proteases of host neutrophils.

Another object of the invention is to provide an antibody fragment based antifungal conjugate selectively targeting *Candida* spp. with high specificity and reduced off-target toxicity.

Yet another object of the invention is to provide an antibody fragment based antifungal conjugate comprising of camelid VHH selectively targeting *Candida* spp. with modified amino acid sequences to increase their similarity to antibody variants produced naturally in humans, thereby, reducing the chance of eliciting an immune response in human host against the antifungal molecule.

Yet another object of the invention is to provide an antibody fragment based antifungal conjugate selectively targeting *Candida* spp. which is a non-toxic prodrug and gets activated only when exposed to pathogenic *Candida* spp. after cleavage of protease cleavage sequence of the antibody fragment based antifungal conjugate by membrane, cell wall associated, or secreted proteases of *Candida* spp., or host neutrophil proteases, thus causing less host toxicity or off-target toxicity due to the antimicrobial peptide.

Yet another object of the invention is to provide an antibody fragment based antifungal conjugate selectively targeting *Candida* spp. which can be easily manipulated for generating next generation of conjugates in case of emergence of drug-resistant forms of the pathogen, wherein, the antimicrobial peptide can be changed either by mutations or can be replaced with more toxic peptides, the protease cleavage sequence can be replaced, the linker can be replaced, and the VHH can be replaced to recognize mutated pathogen more efficiently.

SUMMARY OF THE INVENTION

In the main embodiment, the invention provides a novel antibody fragment based antifungal conjugate selectively targeting *Candida* spp. comprising of at least one antimicrobial peptide at one end of the conjugate either on the C or the N terminal end, more preferably, antimicrobial peptide belonging to the group comprising of cationic histidine-rich antimicrobial peptides, mucin family of proteins, or human defensins; an antibody fragment at the other end of the conjugate, preferably a camelid heavy chain antibody variable region fragment (VHH), specific against the antigen of *Candida* spp. selected from the group consisting surface antigen, and extracellular matrix antigen of biofilm; at least one signal protease cleavage sequence susceptible to cleavage by proteases selected from the group consisting of membrane, cell wall associated, or secreted proteases of *Candida* spp., or host neutrophil proteases; and at least one flexible polypeptide linker. The signal protease cleavage sequence and the flexible polypeptide linker are in tandem with each other and placed in between the antimicrobial peptide and the antibody. The in vitro MIC-99 (minimal inhibitory concentration to kill 99% microorganisms) of the conjugate against *Candida* spp., more specifically, against *C. albicans, C. tropicalis, C. krusei, C. parasilopsis* and *C. glabratais* in the range of 0.2-0.3 μM, more specifically, 250 nM.

The invention relates to a novel antibody fragment based antifungal conjugate selectively targeting *Candida* spp., wherein, said conjugate acts a prodrug and gets activated only upon interaction with pathogenic *Candida* spp. This makes said conjugate less toxic to host cells being administered with said conjugate for treating infections caused by *Candida* spp. Moreover, the VHH targeting *Candida* spp. is humanized by mutating amino acid sequence to reduce chance of eliciting an immune response in human host against the antifungal molecule. The VHH targets the extracellular matrix enolase present on the surface of and in the biofilms of *Candida* spp., thereby enabling the antibody fragment based antifungal conjugate to bind directly to the pathogen surface and the biofilms to assert antimicrobial properties against Candid spp. increasing its efficacy.

The invention also relates to an antibody fragment based antifungal conjugate selectively targeting *Candida* spp., which can be easily manipulated by replacement/mutation of components of said conjugate, wherein, the antimicrobial peptide can be changed by mutation or replaced with more toxic peptides, the protease cleavage sequence can be replaced, the linker can be replaced, and the VHH can be replaced which enables development of novel antimicrobial peptide and antibody conjugate which are efficient to deal with drug-resistance in *Candida* spp.

The antibody fragment based antifungal conjugate can constitute pharmaceutical compositions for topical application, systemic delivery, or oral consumption. Further, the antibody fragment based antifungal conjugate can constitute formulations for coating medical implants to reduce infections.

BRIEF DESCRIPTION OF THE DRAWING(S)

The object of the invention may be understood in more details and more particularly description of the invention briefly summarized above by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

Figure 2A:
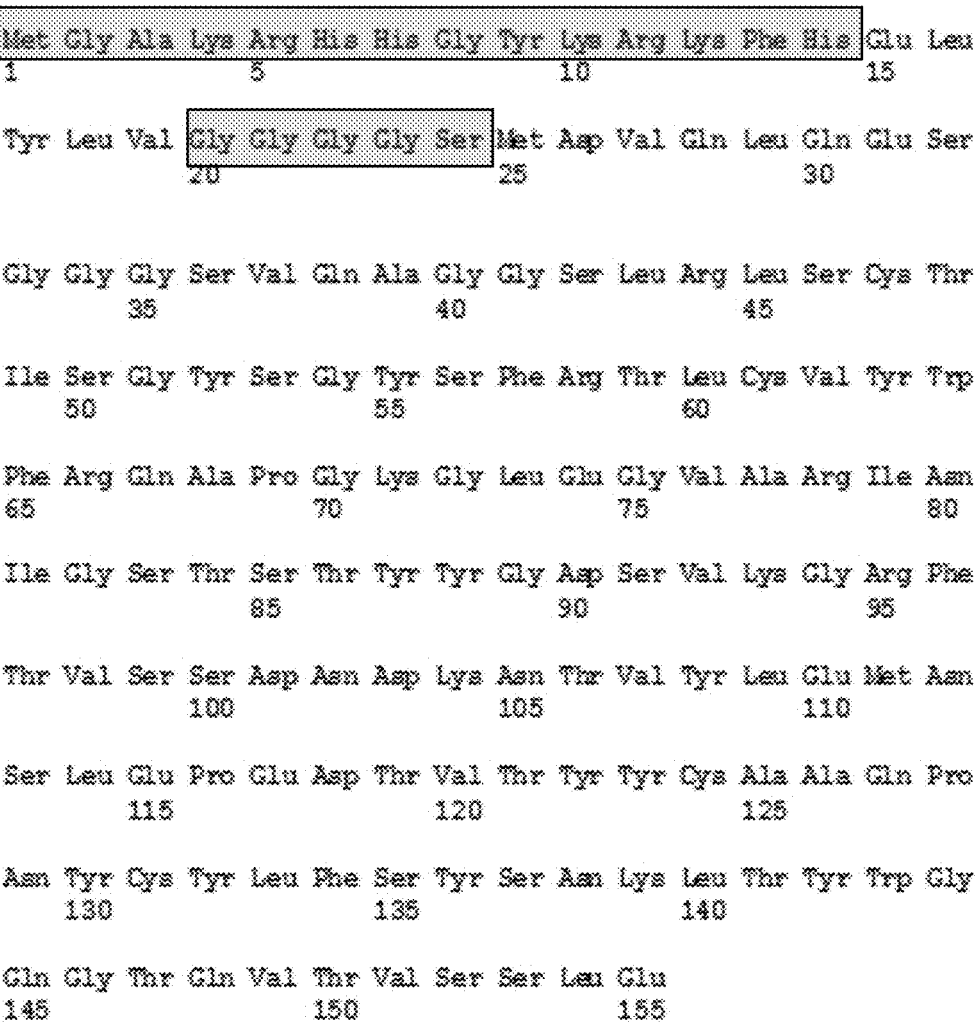
Figures 3A, 3B, 3C, 4, 5:
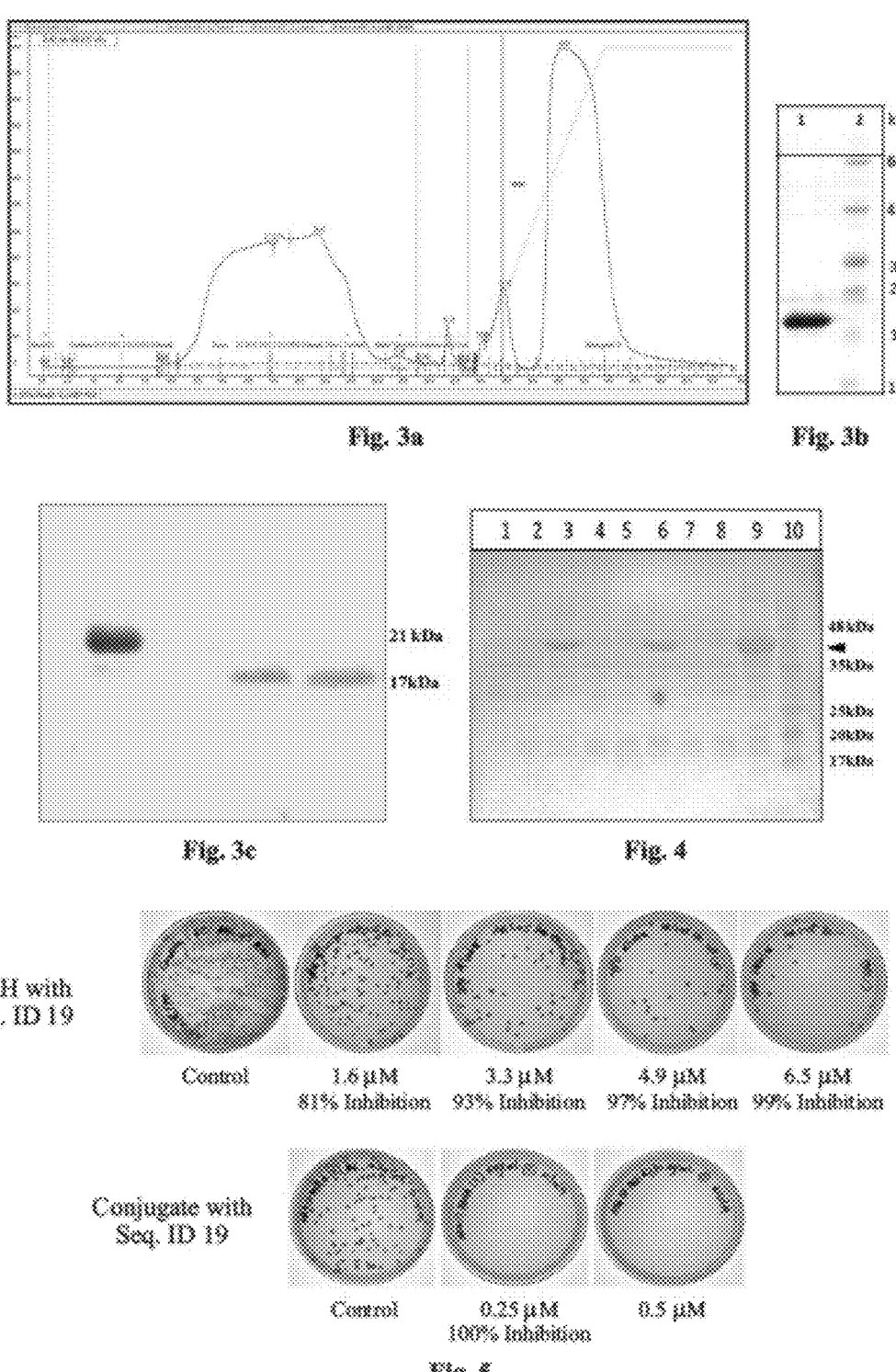

FIG. 1*a* is a schematic of the antibody fragment based antifungal conjugate (100) depicting the cleavage of the conjugate (100) at the protease cleavage site (103) separating antimicrobial peptide (101) and the antibody (102);

FIG. 1*b* is a schematic depicting the mode of action of the antibody fragment based antifungal conjugate (100) at the surface of the pathogen cell membrane (104) by membrane or cell wall associated proteases (105);

FIG. 1*c* is a schematic depicting the mode of action of the antibody fragment based antifungal conjugate (100) at the vicinity of the pathogen by proteases secreted by the pathogen (105);

FIG. 1*d* is a schematic depicting the mode of action of the antibody fragment based antifungal conjugate (100) on host neutrophil ingested pathogen by host neutrophil specific proteases (105);

FIG. 2*a* provides the amino acid sequence of antibody fragment based antifungal conjugate with amino acid sequence represented by Seq. ID 19;

FIG. 2*b* provides the amino acid sequence of antibody fragment based antifungal conjugate with amino acid sequence represented by Seq. ID 20;

FIG. 3*a* depicts achromatogram that shows affinity purification by Ni-NTA (1st round) of conjugate Seq. ID 19 from solubilized inclusion bodies and purified using AKTA-prime plus purification system;

FIG. 3*b* depicts SDS-PAGE image of conjugate Seq. ID 19 purified from solubilized inclusion bodies and purified using AKTA-prime plus purification system;

FIG. 3*c* depict Western blot using the His tagged Seq. ID 9 as the primary antibody and the anti His secondary antibody with cell lysates of *E. coli* strain E2B (Rosetta Gami2 DE3) expressing empty pET vector uninduced in lane 1, and pET vector containing the *Candida Enolase* gene (NCBI No GenBank: M93712.1) uninduced in lane 2 and induced in lane 3; cell lysates of *E. coli* strain C41(DE3) expressing empty pET vector uninduced in lane 4, and pET vector containing the *Candida Enolase* gene uninduced in lane Sand induced in lane 6; cell lysates of *E. coli* strain BL21(DE3) expressing empty pET vector uninduced in lane 7, and the pET vector containing the *Candida Enolase* gene uninduced in lane 8 and induced in lane 9; and marker peptides mix in lane 10;

FIG. 4 is a representative image of SDS PAGE of lysates from *E. coli* expressing the antibody fragment based antifungal conjugate represented by Seq. ID 19 (lane 1) and lysates of *Candida albicans* treated with purified Seq. ID 19 were compared by analysis for the VHH of Seq. ID 9 after 1 hour (lane 2) and 2 hour (lane 3); and FIG. 5 is representative microbiological agar-plate assay to determine MIC-99 of purified Seq. ID19 and Seq. ID 9.

DETAILED DESCRIPTION OF THE INVENTION

The present invention now will be described hereinafter with reference to the detailed description, in which some, but not all embodiments of the invention are indicated. Indeed, the invention may be embodied in many different forms and should not be construed as limited to the embodiments set forth herein; rather, these embodiments are provided so that this disclosure will satisfy applicable legal requirements. The present invention is described fully herein with non-limiting embodiments and exemplary experimentation.

Definitions

The term "antibody fragment" as used herein refers to polypeptides or proteins that bind to specific antigens. It also means immunoglobulins, not limited to polyclonal, monoclonal, chimeric, humanized antibodies, Fab fragments, F(ab')2 fragments and likewise.

The term "antifungal conjugate" as used herein refers to a molecule which shows antimicrobial properties against fungi including single cellular fungi, multicellular fungi, yeast, molds, filamentous fungi, non-filamentous fungi, and other types of fungi.

The term "antimicrobial peptide" as used herein refers to a polymer of amino acid residues typically ranging in length from 10 to about 50 which show antimicrobial properties by associating with membranes of microorganisms and causing membrane permeabilization, thereby killing the microorganisms.

The term "MIC" as used herein refers to minimal inhibitory concentration.

The term "MIC-99" as used herein refers to minimal inhibitory concentration for killing 99% microorganisms.

The term "next generation" as used herein refers to product that has been developed using latest technology to replace existing less efficient form of the drug.

The term "prodrug" as used herein refers to a compound that, after administration, is metabolized (i.e., converted within the body) into a pharmacologically active drug.

The term "in tandem" as used herein refers to one behind another. A sequence in tandem with another is adjacent sequences in continuation.

The term "VHH" as used herein refers to an antigen binding fragment of antibody derived from camels which is composed only of fragments of heavy chains and does not comprise any light chains; it is also called as nanobody. Typically, an IgG antibody comprises two heavy chains and two light chains. Each heavy chain comprises a variable region (encoded by VHH, D and J elements) and a constant region.

The term "virulent protease" as used herein refers to proteases naturally produced by pathogens to attack their host cells and aids in pathogenicity.

The company AbGenics Lifesciences Pvt. Ltd. has developed new generation of antibody fragment based antimicrobial conjugates known by the trademark AbTids® for providing a solution to management of drug-resistant *Candida* spp.

The genus *Candida* represents a highly heterogeneous group of >50 known species. *Candida* species are found as normal flora in healthy individuals and are known to cause opportunistic infections with high rates of mortality, especially in immunocompromised individuals. *Candida* spp. cause systemic diseases which are the fourth leading cause of nosocomial bloodstream infections in modern hospitals. Nevertheless, >90% of the invasive *Candida* infections are caused by *C. albicans, C. glabrata, C. parapsilopsis, C. tropicalis,* or *C. krusei* in many parts of the world.

Therefore, the main embodiment of the present invention provides a novel antibody fragment based antifungal conjugate, selectively targeting *Candida* spp., comprising of:

at least one antimicrobial peptide at one end of the conjugate belonging to the group comprising of cationic histidine-rich antimicrobial peptides, preferably Histatin family of peptides, more preferably, the active fragment of human Histatin-5 represented by amino acid sequence Seq. ID 1, and Seq. ID 2 as listed in Table 1; mucin family of proteins Mucin 1-22, preferably human Mucin 7 represented by amino acid sequence Seq. ID 3, and Seq. ID 4 as listed in Table 1; and human beta defensins, preferably, amino acid sequence Seq. ID 5 as listed in Table 1;

at least one antibody fragment at the other end of the conjugate, preferably, a camelid heavy chain antibody variable region fragment (VHH) targeting antigen present on the cell walls and biofilms of *Candida* spp., more preferably, enolase extracellular matrix antigen, that is also a virulent protease wherein, the sequence of the VHH is selected from the group of amino acid sequences Seq. ID. 6, Seq. ID 7, Seq. ID. 8, and Seq. ID 9 as listed in Table 1, preferably, Seq. ID. 9;

at least one signal protease cleavage sequence susceptible to proteases selected from the group consisting of membrane proteases, cell wall associated proteases, or secreted proteases of *Candida* spp., or proteases of host neutrophils; wherein, the protease specific cleavage sequence is susceptible to cleavage by proteases selected from the group consisting of *Candida* spp. specific secreted aspartyl proteinases (SAP), a secreted virulent protease, preferably, Seq. ID 10 or Seq. ID 1 las listed in Table 1 susceptible to cleavage by SAP1; membrane or cell wall associated proteases of *Candida* spp. preferably, Seq. ID 12 as listed in Table 1 susceptible to cleavage by *Candida* spp. specific signal peptidase 3; and by host neutrophil proteases, preferably Seq. ID 13 as listed in Table 1 susceptible to cleavage by Elastase, Proteinase 3, Matrix metalloproteinases 1 & 13, Thrombin and Activated protein C; or a combination thereof; and at least one flexible polypeptide linker tandem to the protease cleavage sequence, wherein, the linker is selected from the amino acid sequence with Glycine and Serine in tandem with the formula $\{(Gly)_4Ser\}_n$, where n is 1-9, preferably Seq. ID 14, or Seq. ID 15; or from amino acid sequence represented by Seq. ID16 where Glutamic acid can be substituted with Aspartate (D), or from Lysine rich sequences as represented by Seq. ID 17 or Seq. ID 18 or a combination thereof.

TABLE 1

List of amino acid sequences

| Sequence ID no. | Amino acid sequence |
| --- | --- |
| Amino acid sequences of antimicrobial peptide | |
| 1 | Met Xaa Ala Lys Arg His HisGly Tyr Lys Arg Lys Phe His XaaXaa<br>wherein "Xaa" is any amino acid |
| 2 | Ala Lys Arg His HisGly Tyr Lys Arg Lys Phe His |
| 3 | XaaXaaLeuAlaHisGlnLysProPheIleArgLysSer TyrLysCysLeuHisLysArgCysArgXaaXaa<br>wherein "Xaa" is any amino acid |
| 4 | GlyCysLeuAlaHisGlnLysProPheIleArgLysSer TyrLysCysLeuHisLysArgCysArg |
| 5 | GlyIleGlyAspProValThrCysLeuLysSerGlyAla IleCysHisProValPheCysProArgArgTyrLysGln IleGlyThrCysGlyLeuProGlyThrLysCysCysLys LysPro |
| Amino acid sequences of Camelid heavy chain antibody variable region fragment (VHH) specific to _Candida_ spp. | |
| 6 | MetAlaAspValGlnLeuGlnGluSerGlyGlyGlySer ValGlnAlaGlyGlySerLeuArgLeuSerCysThrIle SerGlyTyrSerGlyTyrSerPheArgThrLeuCysValTyrTrpPheArgGlnAlaProGlyLysGluArgGluGly ValAlaArgIleAsnIleGlySerThrSerThrTyrTyr GlyAspSerValLysGlyArgPheThrValSerSerAsp AsnAspLysAsnThrValTyrLeuGluMetAsnSerLeu GluProGluAspThrValThrTyrTyrCysAlaAlaGln ProAsnTyrCysTyrLeuPheSerTyrSerAsnLysLeu ThrTyrTrpGlyGlnGlyThrGlnValThrValSerSer |
| 7 | MetAspValGlnLeuGlnGluSerGlyGlyGlyLeuVal GlnProGlyGlySerLeuArgLeuSerCysAlaThrSer GlyPheThrPheAsnSerTyrTrpMetTyrTrpValArg GlnAlaProGlyLysGlyProGluTrpValAlaArgIle AsnThrArgThrProArgIleThrTyrThrAspSerVal LysGlyArgPheThrIleSerArgAspAsnAlaLysAsn ThrLeuTyrLeuGlnMetAsnSerLeuLysProGluAsp ThrAlaLeuTyrTyrCysThrThrAsnArgAsnArgVal ValGlyGlyGlyThrGlnValThrValSerSer |
| 8 | MetAspValGlnLeuGlnGluSerGlyGlyGlySerVal GlnAlaGlyGlySerLeuArgLeuSerCysValAlaSer GlyValThrTyrSerProTyrTyrCysMetGlyTrpPhe ArgGlyGlnGluArgGluAlaValAlaSerIleThrIle GlyArgIleGlyGlyGlyGlyThr PheValAlaAspSerValLysGlyArgPheThrIleSer GlnAspAlaAlaLysAsnSerAlaTyrLeuGlnLeuAsn SerLeuArgProGluAspSerAlaIleTyrTyrCysAla AlaGlyValGlyTyrCysTyrThrArgArgLeuAspTyr AspHisTrpGlyTyrGlyThrGlnValThrValSerSer |
| 9 | MetAspValGlnLeuGlnGluSerGlyGlyGlySerVal GlnAlaGlyGlySerLeuArgLeuSerCysThrIleSer GlyTyrSerGlyTyrSerPheArgThrLeuCysValTyr TrpPheArgGlnAlaProGlyLysGlyLeuGluGlyVal AlaArgIleAsnIleGlySerThrSerThrTyrTyrGly AspSerValLysGlyArgPheThrValSerSerAspAsn AspLysAsnThrValTyrLeuGluMetAsnSerLeuGlu ProGluAspThrValThrTyrTyrCysAlaAlaGlnPro AsnTyrCysTyrLeuPheSerTyrSerAsnLysLeuThr TyrTrpGlyGlnGlyThrGlnValThrValSerSer |
| Amino acid sequences of Protease cleavage sequence | |
| 10 | Glu Leu Tyr Leu Val |
| 11 | Leu Val Glu Leu Leu Tyr Leu |

TABLE 1-continued

List of amino acid sequences

| Sequence ID no. | Amino acid sequence |
| --- | --- |
| 12 | Lys Arg Glu Ala |
| 13 | Asn Ala Thr Leu Asp Pro Arg Ser Phe Leu Leu Arg Asn |
| Amino acid sequences of flexible linker peptides | |
| 14 | GlyGlyGlyGly Ser |
| 15 | GlyGlyGlyGly Ser GlyGlyGlyGly Ser |
| 16 | Glu GluGlyGluPhe Ser Glu Ala Arg<br>Where Glu is Glu (E) or Asp (D) |
| 17 | Gly Ser Ala Asp Asp Ala Lys Lys Asp Ala Ala Lys Lys Asp Gly Lys Ser |
| 18 | Ser Ser Ala Asp Asp Ala Lys Lys Asp Ala Ala Lys Lys Asp Asp Ala Lys Lys Asp Ala |

The invention provides an antibody fragment based anti-fungal conjugate Seq. ID 19 having in vitro MIC-99 of the conjugate against _Candida_ spp. in the range of 0.2 µM-0.3 µM, more specifically, 0.25 µM or 250 nM.

The most challenging clinical problem is the rapidly growing resistance of _Candida_ spp. Biofilm production is one of the most important factors in developing high level of antimicrobial resistance in Candid spp. Most of the diseases caused by _Candida_ spp. are due to biofilm formation. Biofilms are the group of microorganisms that are embedded in an extracellular matrix, forming a complex three-dimensional architecture on biotic and abiotic surfaces. Biofilms are genetically resistant to antifungal agents including amphotericin B and fluconazole. Biofilms prevent the access of the drugs to the pathogens and consequently these fungi become drug resistant that increases the morbidity and mortality of the infected patients. As currently available antifungals have minimal activity against biofilms, new drugs to treat these recalcitrant infections are urgently needed. Peptide-based therapeutics to treat drug resistant pathogens might be an alternative to conventional antibiotics.

One of the most potent salivary peptides called Histatin 5 is a cationic histidine-rich peptide present in humans and higher primates and has both antibacterial and antifungal activity. Salivary innate immunity is the first line of defense against pathogens in the oral cavity. Histatin is normally present in the oral cavity. The sequence of Histatin-5 used is conserved in Humans, Chimpanzee and Gorilla. It has 83.8% homology to _Homo sapiens,_ 80.4 to Chimpanzees and 70% with Gorilla. The mode of action has been demonstrated to be by internalization followed by intercalation with the DNA or by membrane disruption resulting in leakage from the cells and non-energy dependent lysis. However, such broad-spectrum peptide needs to be diligently inserted into an antimicrobial peptide conjugate to control its non-specific toxicity.

Similarly, mucins, the primary structural components of mucus that creates its viscoelastic properties, are critical components of the gel layer that protect against invading pathogens. Different types of mucins exist throughout the body in various locations. In the oral cavity, decreased salivary flow is linked to the increased incidence of candidiasis and dental caries, which could be caused by reduced levels of salivary mucins. Mucins identified so far are Mucin 1-22, of which Mucin 7 is found in the oral cavity and has anti-*Candida* properties.

Hence, an important aspect of the present invention is to design a novel antibody fragment based antifungal conjugate targeting *Candida* spp. capable to assert antifungal properties on *Candida* biofilms as well. Therefore, the present invention provides a novel antibody fragment based antifungal conjugate, comprising of at least one antimicrobial peptide at one end of the conjugate either on the C or the N terminal end, at least one antibody fragment at the other end of the fragment, at least one protease cleavage sequence, and at least one flexible polypeptide linker, wherein, said antimicrobial peptide belongs to group comprising of cationic histidine-rich antimicrobial peptides, Histatin family of peptides, more preferably, Histatin-5; mucin family of proteins Mucin1-22, preferably, Mucin 7; and human beta defensins. The antimicrobial peptides are derived from Human histatin and mucin amino acid sequence, to reduce any unwanted immunogenic reaction from human host of administration of the antibody fragment based antifungal conjugate for treatment.

Hence, another aspect of the present invention is to provide a novel antibody fragment based antifungal conjugate targeting *Candida* spp. which has the ability to bind to the surface of individual microbes and their biofilms and assert antifungal properties. Accordingly, the invention provides an antibody fragment based antifungal conjugate, comprising of at least at least one antibody specifically recognizing biofilm abundant antigens, more specifically, enolase. Enolase is secreted by *Candida* spp. as a virulent protease and is present in extracellular matrix of biofilms. It has also been shown that *C. albicans* enolase is an immunodominant antigen. Hence, directing the antifungal conjugate by anti-enolase VHH enables the conjugate to bind to the surface of and to the biofilms of *Candida* spp. successfully, thereby enabling it to assert the antifungal properties of the antimicrobial peptide. Moreover, it is essential to ensure target specific activity of the conjugate which is non-toxic to host. The antifungal conjugate is activated only after it encounters the target pathogen. To remove the toxic effect at undesired place, the antimicrobial peptide is fused to a larger antibody fragment that is wrapped around it, reducing its toxic effects both during the bacterial drug production stage and the therapeutic application stage. The antibody is specific to the pathogen which targets the antimicrobial peptide and the antibody conjugate to the surface of the pathogen, thereby reducing non-target action of the antimicrobial peptide. Additionally, the VHH targeting *Candida* spp. may be humanized by mutating amino acid sequence to reduce chance of eliciting an immune response in human host against the antifungal molecule.

Additionally, the invention provides an antibody fragment based antifungal conjugate, which acts as a prodrug and is activated only upon encountering the pathogen to reduce non-toxicity to host and non-target activation. Therefore, the invention provides an antibody fragment based antifungal conjugate, comprising of at least one antimicrobial peptide at one end of the conjugate either on the C or the N terminal end, at least one antibody fragment (VHH) at the other end of the fragment, at least one protease cleavage sequence, and at least one flexible polypeptide linker, wherein, the protease cleavage specific sequence is cleaved upon interaction with membrane, cell wall associated, or secreted protease of *Candida* spp., or host neutrophil specific proteases, more preferably, SAP1 of *Candida* spp. The protease cleavage sequence and the flexible polypeptide linker sequence are placed in tandem in between the antimicrobial peptide and antibody fragment. The conjugate is a non-toxic prodrug and gets activated only upon interaction of the VHH of the conjugate with *Candida* spp., thereby initiating a cascade of reactions leading to cleavage of the protease cleavage site of the conjugate releasing the antimicrobial peptide from the conjugate to act against the *Candida* spp. The antimicrobial peptide is now released from the prodrug and is capable to assert antimicrobial properties against the pathogen. Optionally, the protease cleavage sequence may be specific to host neutrophil proteases, to clear neutrophil ingested pathogen. Optionally, a combination of antibody fragment based antifungal conjugate comprising of conjugates having pathogen specific protease cleavage sequence, and conjugates having host neutrophil specific proteases cleavage sequence can be used to defend against both free pathogens and neutrophil ingested pathogens.

The three most significant extracellular hydrolytic enzymes produced by *C. albicans* are the secreted aspartyl proteinases (SAP), phospholipase B enzymes, and lipases. Of these, the SAP proteins, encoded by a family of 10 SAP genes, have been the most comprehensively studied as key virulence determinants of *C. albicans*. *C. albicans* is not the only *Candida* species known to produce extracellular proteinases. Many of the pathogenic *Candida* species have been shown to possess SAP genes, hence SAP is common to many pathogenic *Candida* spp.

Example 1

Antibody Fragment Based Antifungal Conjugate Design and its Mode of Action Against Pathogen As depicted in FIG. 1*a* the antibody fragment based antifungal conjugate (100) comprises of antimicrobial peptide (101) followed by a linker (103) sequence and a pathogen specific antibody fragment (102). The linker (103) additional comprises of a small protease cleavage sequence (103) susceptible to cleavage by pathogen specific proteases (105) such as membrane, cell wall associated, or secreted proteases, or are host neutrophil specific proteases (105). The antibody fragment (102) preferably a camelid VHH fragment targeting the pathogen surface or extracellular matrix antigen. The conjugate (100) is a prodrug which on encountering the pathogen initiates a cascade of reactions leading to cleavage of the protease cleavage site (103) and releases the antimicrobial peptide (101) from the antibody fragment (102).

The antibody fragment based antifungal conjugate (100) may act against the pathogen in three different modes based on the kind of protease cleavage sequence (103).

Mode 1 is depicted in FIG. 1*b*, where the protease cleavage sequence (103) of antibody fragment based antifungal conjugate (100) is specific to membrane or cell wall associated proteases (105). The antibody fragment based antifungal conjugate (100) targets the pathogen in the host organism, because of the affinity of the antibody fragment (102) to the antigen on the pathogen, which upon coming in contact with the pathogen membrane or cell wall (104) is susceptible to cleavage by membrane or cell wall associated proteases (105), thereby releasing the antimicrobial peptide (101).

Mode 2 is depicted in FIG. 1*c*, where the protease cleavage sequence (103) of antibody fragment based antifungal conjugate (100) is specific to proteases secreted by pathogens (105). The antibody fragment based antifungal conjugate (100) targets the pathogen in the host organism which upon coming in vicinity of the pathogen is susceptible to cleavage by pathogen secreted proteases, thereby releasing the antimicrobial peptide (101).

Mode 3 is depicted in FIG. 1*d*, where the protease cleavage sequence (103) of antibody fragment based antifungal conjugate (100) is specific to host neutrophil specific proteases (105). The antibody fragment based antifungal conjugate (100) is internalized by the host neutrophils (106) and inside the neutrophil the antibody fragment based antifungal conjugate (100) targets neutrophil ingested pathogen which upon being internalized by host neutrophil is susceptible to cleavage by host neutrophils proteases (105), thereby releasing the antimicrobial peptide (101). In all the above three modes, once the antimicrobial peptide is released from the antibody fragment based antifungal conjugate, the peptide can assert its antimicrobial properties against the pathogen.

The antibody fragment based antifungal conjugate specific against *Candida albicans* comprises of amino acids represented by Seq. ID 19 and Seq. ID 20,

```
Seq. ID 19:
Met Gly Ala Lys Arg His HisGly Tyr Lys Arg Lys

Phe His Glu Leu Tyr Leu Val GlyGlyGlyGly Ser

Met Asp Val Gln Leu Gln Glu Ser GlyGlyGly Ser

Val Gln Ala GlyGly Ser Leu Arg Leu Ser CysThr

Ile Ser Gly Tyr Ser Gly Tyr Ser Phe Arg Thr

Leu Cys Val Tyr TrpPhe Arg Gln Ala Pro Gly Lys

Gly Leu Glu Gly Val Ala Arg Ile Asn Ile Gly

Ser Thr Ser Thr Tyr TyrGly Asp Ser Val Lys Gly

Arg PheThr Val Ser Ser Asp Asn Asp Lys AsnThr

Val Tyr Leu Glu Met Asn Ser Leu Glu Pro Glu

Asp Thr Val Thr Tyr TyrCys Ala Ala Gln Pro Asn

Tyr Cys Tyr Leu Phe Ser Tyr Ser Asn Lys Leu

Thr Tyr TrpGly Gln GlyThr Gln Val Thr Val Ser

Ser Leu Glu;
and

Seq. ID 20:
Met GlyGlyCys Leu Ala His Gln Lys Pro Phe Ile

Arg Lys Ser Tyr Lys Cys Leu His Lys Arg Cys

Arg Lys Arg Glu Ala GlyGlyGlyGly Ser GlyGly

GlyGly Ser Met Asp Val Gln Leu Gln Glu Ser

GlyGlyGly Ser Val Gln Ala GlyGly Ser Leu Arg

Leu Ser Cys Val Ala Ser Gly Val Thr Tyr Ser

Pro Tyr TyrCys Met GlyTrpPhe Arg Gly Gln Glu

Arg Glu Ala Val Ala Ser Ile Thr Ile Gly Arg

Ile GlyGlyGlyGlyThrPhe Val Ala Asp Ser Val

Lys Gly Arg PheThr Ile Ser Gln Asp Ala Ala

Lys Asn Ser Ala Tyr Leu Gln Leu Asn Ser Leu

Arg Pro Glu Asp Ser Ala Ile Tyr TyrCys Ala
```

14

```
-continued
AlaGly Val Gly Tyr Cys Tyr Thr Arg Arg Leu

Asp Tyr Asp His TrpGly Tyr GlyThr Gln Val

Thr Val Ser Ser Leu Glu
```

As depicted in FIG. 2*a*, the Seq. ID 19 comprises of 155 amino acids of which amino acids 1-14 correspond to the antimicrobial peptide, human Histatin 5 active region, amino acids 15-19 (ELYLV) is the SAP1 specific cleavage sequence, amino acid sequence 20-24 correspond to the linker with Glycine and Serine residues (Gly)₄Ser in tandem, and amino acid sequence 25-155 is Seq. ID 9 which is humanized Camelid heavy chain antibody variable region fragment (VHH) specific to *Candida albicans* antigen enolase.

As depicted in FIG. 2*b*, the Seq. ID 20 comprises of 165 amino acids of which amino acids 1-24 correspond to the antimicrobial peptide, Mucin 7, amino acids 25-28 (KREA) is the fungal signal peptidase 3 specific cleavage sequence, amino acid sequence 29-38 correspond to the linker with Glycine and Serine residues((Gly)₄Ser)₂ in tandem, and amino acid sequence 38-165 is Seq. ID 8 which is Camelid heavy chain antibody variable region fragment (VHH) specific to *Candida albicans* surface antigen to which it shows a strong binding.

The human Histatin 5 active region amino sequence is AKRHHGYKRKFH to with two amino acids at the N terminal and two amino acids at the C terminal end may be optionally added to give stability to the peptide after it has been released from the conjugate and also to facilitate fusion to the antibody during the cloning steps.

Example 2

Anti-*Candida* Camelid Heavy Chain Antibody Variable Region Fragment (VHH)

Heavy chain antibody based anti-*Candida* molecules was developed with the ability to kill *Candida* spp. that possibly disrupt biofilms as well. For this purpose, camels were immunized with the extracts of *Candida albicans* isolated from clinical samples. The antibody library was prepared in a phage display vector in *E. coli* and hits were isolated after panning against microbial cell wall components and strong binders assayed for their *Candida* neutralizing ability.

Camelid monoclonal antibody fragments are derived from single heavy chain antibody molecules derived from camels, with low immune signature in humans, extremely small (15 kDa), with excellent stability and tissue penetrability properties. These antibodies do not need cold chain for transportation and remain stable for years at room temperature, a property, that can be exploited to develop and formulate stable antimicrobials. Furthermore, being small, they can be engineered to add value, have the ability of deep tissue penetration and disruption of biofilms. Four antibodies were isolated and sequenced with the Seq. ID 6, Seq. ID 7, Seq. ID 8, and Seq. ID 9. These antimicrobial antibodies can be used to control topical as well as invasive *Candida* infections.

The target for antimicrobial antibodies with amino acid sequence represented by Seq. ID 6 was identified to be extracellular matrix enolase present on the surface of the pathogen as a virulent protease also present in biofilms of *Candida* spp. and is an important immune antigen for *Candida* biofilms. This antibody was used as a backbone to produce the antimicrobial peptide antibody conjugate.

Camelid antibodies have a low immune signature but have been shown to elicit an anti-camel immune response when applied in high doses. To overcome this problem, the antibody may be optionally humanized by replacing amino acids of antibodies by mutation.

Accordingly, anti-*Candida* antibody with amino acid sequence represented by Seq. ID 6 was humanized by mutation to generate anti-*Candida* antibody with amino acid sequence represented by Seq. ID 9, wherein, the Glutamic acid (E) at position 49 of was replaced by Glycine (G), and the Arginine (R) at position 50 was replaced with Leucine (L). Hence, VHH with Seq. ID 9 is a humanized form VHH Seq. ID 6. This VHH with Seq. ID 9 is expected to have a low immune signature and can be used for large dose parenteral applications as well.

Example 3

Expression, Purification, and Specificity Test of Antibody Fragment Based Antifungal Conjugates Conjugate with Seq. ID 19 was expressed in pET28c+ vector in the *E. coli* BL21(DE3) system as inclusion bodies, solubilized and purified using metal affinity and ion exchange chromatography as depicted in FIG. 3a and the Purified final product as depicted by SDS PAGE in FIG. 3b and used for further analysis.

The antibody fragment based antifungal conjugates comprise of VHH fragments against *Candida* specific enolase. Hence, to confirm the specificity of the VHH fragments towards enolase the following experiment was conducted. VHH fragment represented by Seq. ID 9 was expressed in *E. coli* strains, E2B (Rosetta Gami2 DE3), C41 (DE3), and BL21(DE3), using a suitable His-vector and isolated. The *Candida enolase* gene (NCBI No GenBank: M93712.1) 44 kDa, was expressed in a pET expression vector in the above mentioned three strains of *E coli*, the cell lysates were subjected to SDS-PAGE followed by western blotting using the VHH fragment represented by Seq. ID 9 as the primary antibody and anti-His Mouse as secondary antibody and anti-mouse HRP as tertiary antibodies. As depicted in FIG. 3c, strong signal in all the three clones in lanes 3, 6, and 9 of the western blots, confirmed the target to be the *Candida* specific Enolase, the glycolytic enzyme and the immunodominant antigen.

Example 4

The Conjugate is a Prodrug

The antibody fragment based antifungal conjugate which is initially a prodrug and inactive because the antimicrobial peptide is partially or wholly enclosed by the antibody component.

As depicted in FIG. 4, the purified antibody fragment based antifungal conjugate with Seq. ID 19 was compared to antibody fragment based antifungal conjugate with Seq. ID 19 exposed to pathogen *Candida albicans* and subjected to SDS PAGE analysis using camelid antibody of Seq. ID 9. The purified antibody fragment based antifungal conjugate with Seq. ID 19 (Lane 1) showed larger sized molecule (22 kDa) compared to antibody fragment (17 kDa) based antifungal conjugate with Seq. ID 19 exposed to *Candida albicans* (Lanes 2 and 3). The difference in size was comparable to that of the antimicrobial peptide, Histatin 5 active region of amino acid sequence represented by Seq. ID2. This confirmed that the conjugate was cleaved when it encountered the proteases released by the pathogen thereby releasing Histatin 5 active region.

Example 5

A. Efficiency Test of the VHH Antibody with Seq. ID 9

Purified VHH fragment against *Candida enolase* represented by Seq. ID 9 showed ~99% inhibition of growth of against *C. albicans, C. tropicalis, C. krusei, C. parasilopsis,* and *C. glabrata* with the MIC dose of 125 ug/ml.

TABLE 2

| Efficacy of Seq. ID 9 against different spp. of *Candida* % Growth inhibition* with Seq. ID 9 (125 ug/mL) | |
| --- | --- |
| *Candida albicans* (Lab strain) | 99.81% |
| *Candida albicans* (MTCC 227) | 99.54% |
| *Candida tropicalis* | 99.56% |
| *Candida krusei* | 98.16% |
| *Candida glabrata* | 98.85% |
| *Candida parasilopsis* | 99.50% |

*Individual controls maintained

B. Efficiency Test of the Antibody Fragment Based Antifungal Conjugate with Seq. ID20

Microbiology assays were done with the purified VHH with Seq. ID9 and the antibody fragment based antifungal conjugate of Seq. ID 19 to see their antifungal activity. As depicted in FIG. 5, the MIC-99 of the Seq. ID9VHH fragment alone was found to be 6.5 μM (in anaerobic conditions) but the value was reduced by 20-fold for the conjugate of Seq. ID 19 with value of 0.25 μM.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

I claim:

1. An antibody fragment based antifungal conjugate selectively targeting *Candida* spp., comprising
an antimicrobial peptide at one end of the conjugate,
an antibody fragment at the other end of the conjugate that is a camelid heavy chain antibody variable region fragment (VHH) specific against an antigen of *Candida* spp. selected from the group consisting of surface antigen, and extracellular matrix antigen of *Candida* biofilm,
at least one signal protease cleavage sequence susceptible to cleavage by proteases selected from the group consisting of membrane proteases, cell wall associated proteases, secreted proteases of *Candida* spp., and proteases of host neutrophils; and at least one flexible polypeptide linker in tandem with the signal protease cleavage sequence, with the signal protease cleavage sequence and the polypeptide linker placed in between the antimicrobial peptide and antibody fragment;
wherein,
the amino acid sequence of the conjugate is SEQ ID NO: 19 consisting of antimicrobial peptide of SEQ ID NO: 2, a protease specific cleavage sequence of SEQ ID NO: 10 which is susceptible to cleavage by virulent protease secreted aspartyl proteinase-1 (SAP1) secreted by *Candida* spp., a flexible Glycine Serine linker of SEQ ID NO: 14, and antibody fragment of SEQ ID NO: 9 targeting *Candida* spp. specific enolase which is a virulence factor protease and biofilm specific antigen of *Candida* spp.; and
the in vitro MIC-99 of the conjugate of SEQ ID NO: 19 against *Candida albicans* is 0.25 µm.

2. The antibody fragment based antifungal conjugate as claimed in claim 1, wherein, the VHH of SEQ ID NO: 9 is humanized form of SEQ ID NO: 6 generated by mutating SEQ ID NO: 6 at position 49 from glutamic acid to glycine, and at position 50 from arginine to leucine.

3. The antibody fragment based antifungal conjugate as claimed in claim 1, wherein, the conjugate is in a pharmaceutical composition formulated for topical application, systemic delivery, or oral consumption.

4. The antibody fragment based antifungal conjugate as claimed in claim 1, wherein, the conjugate is in a formulation for coating medical implants to reduce infections.

* * * * *